US011202868B2

(12) United States Patent
Gonzales et al.

(10) Patent No.: US 11,202,868 B2
(45) Date of Patent: Dec. 21, 2021

(54) SAFETY NEEDLE ASSEMBLY

(71) Applicant: TERUMO KABUSHIKI KAISHA, Tokyo (JP)

(72) Inventors: Laurence Gonzales, Binan (PH); Satoshi Kagaya, Nakakoma-gun (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 482 days.

(21) Appl. No.: 15/828,740

(22) Filed: Dec. 1, 2017

(65) Prior Publication Data
US 2018/0085534 A1 Mar. 29, 2018

Related U.S. Application Data

(60) Division of application No. 13/966,892, filed on Aug. 14, 2013, now Pat. No. 9,861,761, which is a
(Continued)

(30) Foreign Application Priority Data

Feb. 14, 2011 (JP) ................................. 2011-028075

(51) Int. Cl.
*A61M 5/32* (2006.01)

(52) U.S. Cl.
CPC ........ *A61M 5/3219* (2013.01); *A61M 5/3216* (2013.01); *A61M 5/3202* (2013.01); *A61M 2005/3217* (2013.01)

(58) Field of Classification Search
CPC .... A61M 5/32; A61M 5/3202; A61M 5/3204; A61M 5/3205; A61M 5/321;
(Continued)

(56) References Cited

U.S. PATENT DOCUMENTS

| | | | | |
|---|---|---|---|---|
| 4,832,696 A | * | 5/1989 | Luther .................. | A61M 5/158 604/164.08 |
| 5,135,509 A | * | 8/1992 | Olliffe .................. | A61M 5/3216 604/192 |

(Continued)

FOREIGN PATENT DOCUMENTS

| | | |
|---|---|---|
| CN | 1520893 A | 8/2004 |
| CN | 1668351 A | 9/2005 |

(Continued)

OTHER PUBLICATIONS

International Search Report (PCT/ISA/210) dated Mar. 6, 2012, by the Japanese Patent Office as the International Searching Authority for International Application No. PCT/JP2012/053136.
(Continued)

*Primary Examiner* — Scott J Medway
(74) *Attorney, Agent, or Firm* — Buchanan Ingersoll & Rooney PC (57) ABSTRACT

The present invention is directed to a safety needle assembly having the high safety and high operability, comprising: a hub; a cannula; a collar; a protector; and a sheath. The sheath includes an opening of housing the cannula; a cannula fixing part of locking the cannula housed in the opening; an attachment part of rotatably supporting the sheath attached to the hub or the collar; and a protrusive stopper which a user pushes by a finger to pivot the sheath thereby to house the cannula in the opening of the sheath. Herein, the stopper is arranged at a vicinity of a central portion of the sheath in a longitudinal direction at the opposite side of the aperture of the opening, or arranged at a portion closer to a distal end side than the central portion of the sheath.

4 Claims, 7 Drawing Sheets

Related U.S. Application Data continuation of application No. PCT/JP2012/053136, filed on Feb. 10, 2012.

(58) Field of Classification Search
CPC .............. A61M 5/3216; A61M 5/3219; A61M 2005/3206; A61M 2005/3217
See application file for complete search history.

(56) References Cited

U.S. PATENT DOCUMENTS

| | | | | |
|---|---|---|---|---|
| 5,188,611 A * | 2/1993 | Orgain | ................ | A61M 5/3216 604/192 |
| 5,462,534 A * | 10/1995 | Debreczeni | ......... | A61M 5/3216 604/192 |
| 5,509,907 A * | 4/1996 | Bevilacqua | ......... | A61M 5/3216 604/192 |
| 5,599,313 A * | 2/1997 | Gyure | ................ | A61M 5/3216 604/111 |
| 5,599,318 A * | 2/1997 | Sweeney | ............. | A61M 5/3216 604/263 |
| 5,623,762 A | 4/1997 | White | | |
| 5,643,219 A | 7/1997 | Burns | | |
| 5,662,617 A * | 9/1997 | Odell | ................ | A61M 5/3216 128/919 |
| 5,669,889 A * | 9/1997 | Gyure | ................ | A61M 5/3216 604/263 |
| 5,733,265 A * | 3/1998 | Bachman | ............ | A61M 5/3216 604/192 |
| 5,746,726 A * | 5/1998 | Sweeney | ............. | A61M 5/3216 604/192 |
| 5,913,846 A * | 6/1999 | Szabo | ................ | A61M 5/3216 128/919 |
| 5,925,020 A * | 7/1999 | Nested | ................ | A61M 5/3275 604/198 |
| 6,042,570 A * | 3/2000 | Bell | ................ | A61M 25/0631 604/192 |
| 6,120,482 A * | 9/2000 | Szabo | ................ | A61M 5/3216 128/919 |
| 6,298,541 B1 | 10/2001 | Newby et al. | | |
| 6,454,746 B1 * | 9/2002 | Bydlon | ................ | A61M 5/3137 604/227 |
| 6,575,941 B1 * | 6/2003 | Mumford | ............ | A61M 5/3216 604/192 |
| 6,582,397 B2 * | 6/2003 | Alesi | ................ | A61M 5/3216 604/110 |
| 6,699,217 B2 * | 3/2004 | Bennett | ............... | A61M 5/3216 128/919 |
| 6,837,877 B2 * | 1/2005 | Zurcher | ................ | A61B 5/153 128/919 |
| 6,984,223 B2 * | 1/2006 | Newby | ............ | A61B 5/150717 604/263 |
| 7,201,736 B2 * | 4/2007 | Hauri | ................ | A61M 5/3216 604/110 |
| 7,316,668 B2 * | 1/2008 | Swenson | ............ | A61M 5/3216 604/192 |
| 7,635,352 B2 * | 12/2009 | Adams | .............. | A61M 25/0618 604/164.08 |
| 8,057,431 B2 * | 11/2011 | Woehr | ................ | A61M 5/3216 604/110 |
| 8,172,809 B2 * | 5/2012 | Ferguson | ......... | A61B 5/150496 604/192 |
| 8,535,274 B2 * | 9/2013 | Hjertman | ............ | A61M 5/3129 604/187 |
| 10,029,049 B2 * | 7/2018 | Bubenik | ............. | A61M 5/3216 |
| 10,639,430 B2 * | 5/2020 | Bubenik | ............. | A61M 5/3202 |
| 2001/0008963 A1 * | 7/2001 | Alesi | .................... | A61M 5/158 604/263 |
| 2003/0181873 A1 | 9/2003 | Swenson | | |
| 2003/0212369 A1 | 11/2003 | Kobayashi | | |
| 2003/0220614 A1 * | 11/2003 | Crawford | ............. | A61M 5/002 604/192 |
| 2007/0265566 A1 | 11/2007 | Simpson et al. | | |
| 2008/0208138 A1 * | 8/2008 | Lim | .................... | A61M 5/3216 604/192 |
| 2008/0306451 A1 | 12/2008 | Woehr et al. | | |
| 2009/0131876 A1 * | 5/2009 | Coyne | .................. | A61M 5/3275 604/198 |
| 2010/0198152 A1 * | 8/2010 | Haindl | ................ | A61M 5/3216 604/110 |
| 2012/0277628 A1 * | 11/2012 | Schraga | ........... | A61B 5/150671 600/576 |
| 2012/0323216 A1 * | 12/2012 | Koh | .................... | A61M 5/3216 604/506 |
| 2013/0331793 A1 * | 12/2013 | Gonzales | ............ | A61M 5/3219 604/192 |
| 2018/0064883 A1 * | 3/2018 | Calvert | ............... | A61M 5/3202 |

FOREIGN PATENT DOCUMENTS

| | | |
|---|---|---|
| EP | 0815888 | 6/1997 |
| JP | 8107933 A | 4/1996 |
| JP | 2000140109 A | 5/2000 |
| JP | 2003275304 A | 9/2003 |
| JP | 2005525198 A | 8/2005 |
| WO | 03097136 A1 | 11/2003 |
| WO | 2008076459 A1 | 6/2008 |
| WO | 2010059502 | 5/2010 |

OTHER PUBLICATIONS

Written Opinion (PCT/ISA/237) dated Mar. 6, 2012, by the Japanese Patent Office as the International Searching Authority for International Application No. PCT/JP2012/053136.

Chinese First Office Action dated Dec. 26, 2014 issued in the corresponding Chinese Patent Application No. 201280006699.1 and English translation (9 pages).

Extended European Search Report dated May 29, 2017 in corresponding European Patent Application No. 12747609.1 May 29, 2017.

* cited by examiner

FIG.9B ns (that is, comprised of a needle and collar, and being detachable to expose the distal end of the
SAFETY NEEDLE ASSEMBLY The present application is a divisional of U.S. application Ser. No. 13/966,892 filed Aug. 14, 2013, which is a continuation of PCT/JP2012/053136 filed Feb. 10, 2012, and claims the benefit of Japanese Application No. JP2011-028075 filed Feb. 14, 2011, the entire content of each of which is incorporated by reference herein.

BACKGROUND OF THE INVENTION

Field of the Invention

The present invention relates to a needle assembly having a safety mechanism (that is, comprised of a needle and attachment parts).

Description of the Related Art

Conventionally, different types of needles such as needles for a hypodermic syringe and a catheter have been applied to a medical tool. Here, a user (such as a health care worker) has to safely handle those needles. Otherwise, if a user erroneously sticks such a needle used for a patient or the like into the user's own body (finger or the like), the user may be infected with a disease.

Herein, there may be a method for preventing such a sting accident from happening, for example, including a means of covering a used needle with a cylindrical cap. However, even in this method, a user may erroneously stick a needle into one of user's fingers holding the cap. Therefore, this method cannot be perfectly safe for preventing a sting accident.

Regarding other methods, for example, Patent Documents 1 and 2 disclose a technique for preventing a sting accident by using a needle assembly comprised of a sheath (or shield) for covering a needle. According to that technique, a user can utilize the needle assembly in the steps of: using a needle for a medical treatment; pivoting a sheath by finger(s) so as to cover the used needle with the sheath; and fixing the state that the used needle is covered by the sheath.

PRIOR ART DOCUMENTS

Patent Documents

Patent Document 1: JP 2000-140109
Patent Document 2: JP 2005-525198

However, it should be noted that the technique disclosed in Patent Document 1 needs large force for using the needle assembly, since there is only a short distance between a fulcrum of the pivoting sheath and a position on the sheath which a user pushes by a finger. This results in the poor operability of the needle assembly.

Further, according to a technique disclosed in Patent Document 2, no stopper which a user pushes by a finger to pivot a sheath is provided with the needle assembly. This also results in the poor operability of the needle assembly.

Accordingly, from the viewpoint of the above mentioned drawbacks, the present invention has been developed so as to provide a safety needle assembly having the high safety and operability.

Means For Solving the Problems

The present invention is directed to a safety needle assembly including a sheath having the following features. That is, the sheath comprises: a hub including a proximal end connecting with a syringe, and a distal end; a cannula having a proximal end connecting with the distal end of the hub, a lumen extending in a longitudinal direction of the cannula, and a distal end; a collar attached to the hub and having a sheath attachment part; a protector covering the distal end of the cannula by being attached to the hub or the collar, and being detachable to expose the distal end of the cannula; an opening partially extending along at least a longitudinal direction of the sheath so as to house the cannula.

The sheath further comprises: a cannula fixing part of locking the cannula housed in the opening; an attachment part rotatably supporting the sheath in a direction of housing the cannula when the protector is detached to expose the distal end of the cannula, the attachment part being attached to the sheath attachment part of the collar; and a protrusive stopper arranged at a vicinity of a central portion of the sheath in a longitudinal direction in which the central portion is located at an opposite side of an aperture of the opening, or arranged at a position closer to the distal end of the sheath than the central portion. Herein, a user's finger pushes the stopper on the sheath so as to house the cannula in the opening.

The above mentioned mechanism allows the safety needle assembly to realize the high safety. Further, the sheath provided with the protrusive stopper arranged at a vicinity of a central portion of the sheath in a longitudinal direction, or arranged at a position closer to the distal end of the sheath than the central portion also allows the safety needle assembly to realize the high operability.

More specifically, the stopper located at the position as described above enables the user to push the stopper on the sheath by a finger at a far position from the fulcrum, allowing a large moment to be generated. This large moment enables the sheath to be pivoted by relatively small force.

Further, the present invention is also directed to a safety needle assembly including a sheath having the following features. That is, the sheath comprises: a hub including a proximal end connecting with a syringe and a distal end; a cannula having a proximal end connecting with the distal end of the hub, a lumen extending in a longitudinal direction, and a distal end; a collar attached to the hub and having a sheath attachment part and a pair of sheath fixing protrusions; a protector covering the distal end of the cannula by being attached to the hub or the collar, and being detachable to expose the distal end of the cannula; and an opening partially extending along at least a longitudinal direction of the sheath so as to house the cannula.

The sheath further comprises: a cannula fixing part comprised of grooves respectively fitting with the pair of sheath fixing protrusions when the cannula is housed in the opening, and a pair of wing walls each of which has a slope arranged inside the wall in a direction from the groove to the proximal end of the sheath; and an attachment part rotatably supporting the sheath in a direction of housing the cannula when the protector is detached to expose the distal end of the cannula, the attachment part being attached to the sheath attachment part of the collar.

The above mentioned mechanism allows the safety needle assembly to realize the high safety. Further, the sheath provided with the pair of wing walls including the grooves and slopes allows the safety needle assembly to realize the high operability. More specifically, the wing wall protruding from the sheath body has flexibility to be easily bended outside. Further, the slopes allow the sheath fixing protrusions located on the collar to be more easily introduced into the grooves. Moreover, the grooves facilitate the sheath fixing protrusions of the collar to be fixed with the sheath.

Accordingly, this construction enables the sheath fixing protrusions located on the collar to be fitted and fixed to the gloves in the wing walls of the sheath, by relatively small force when a user pushes the sheath by a finger.

Further, in the present invention, preferably the sheath comprises a circular recess, and a slope having a plurality of protrusions and recesses with large frictional resistance arranged between the circular recess and the stopper. Herein, the circular recess and the slope are used as a finger guiding region to which a user's finger of operating the sheath contacts, and arranged at a position closer to a proximal end side than the stopper arranged at the opposite side of the aperture of the opening.

The above mentioned construction enables the user to push the sheath at either of the positions at: the circular recess to which a user's finger easily fits, or the slope having a plurality of protrusions and recesses with large friction resistance. Accordingly, this enables the safety needle assembly to realize the high operability.

Further, in the present invention, preferably the sheath comprises a locking tab inside the opening as a cannula fixing part, the locking tab protruding from the side wall of the opening to the inside thereof. Herein, the locking tab passes the cannula introduced in the opening, and then fixes the cannula.

This construction enables the cannula housed inside the opening of the sheath to be fixed by a locking tab which is easily molded. Hereby, the cannula fixing part can be produced at low cost.

Further, in the present invention, an attachment part of the sheath is comprised of cylindrical pins. Herein, the sheath attachment part of the collar is preferably comprised of protruded ears, including a pair of through halls of respectively housing the cylindrical pins, and inside chamfers of receiving the respective cylindrical pins.

According to the above mentioned construction, the ears of the collar respectively have the chamfers inside the ears. Hereby, when the sheath is to be attached to the collar, relatively small force is only needed for attaching the sheath to the collar via the chamfers.

Further, in the present invention, preferably the pair of sheath fixing protrusions located on the collar respectively has a substantially triangle shape and are arranged at the opposite position of the sheath attachment part. Further, preferably the pair of sheath fixing protrusions has grooves respectively fitting with a pair of wing walls of the cannula fixing part.

The above mentioned construction enables the pair of sheath fixing protrusions of the collar to be realized respectively in a simple structure like a substantially triangle shape having a groove.

Effect of the Invention

According to the present invention, a safety needle assembly having both high safety and operability is provided.

EMBODIMENTS FOR CARRYING OUT THE INVENTION

Hereinafter, embodiments for carrying out the present invention will be explained in detail referring to the attached drawings (or appropriately referring to the following descriptions besides the drawings).

Here, a safety needle assembly in the present embodiment is used via connected with a liquid transfer apparatus such as a syringe (hereinafter, simply called "syringe"). Here, the safety needle assembly is packaged by blister packaging or the like which is formed by extending a plastic sheet material. In this case, after treating such a packaged product, a user connects the safety needle assembly with a syringe. Alternatively, in the state being connected with a syringe, the safety needle assembly may be packaged as a product.

Figure 1:
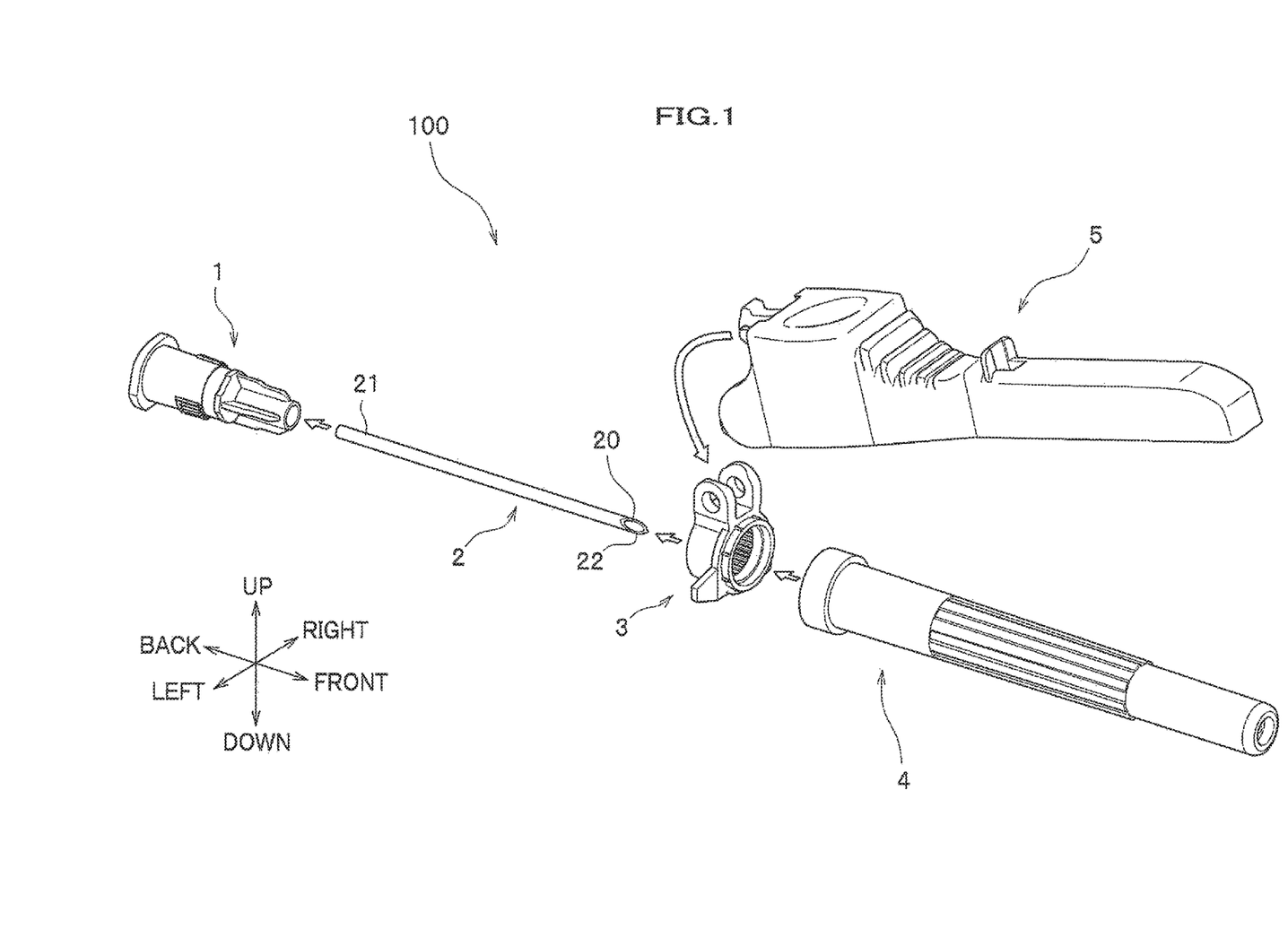
FIG. 1 is an exploded perspective view showing the components of a safety needle assembly in a present embodiment.

First, referring to FIG. 1, the whole construction of the safety needle assembly in the present embodiment will be explained. Note when each component of the assembly is explained, a "direction" described therein is defined by the respective directions in FIG. 1, showing "Up" and "Down", "Front" (or distal end side) and "Back" (or proximal end side), and "Left" and "Right". In other FIGS, the directions are similarly described to those in FIG. 1. Further, it should be noted that the "proximal end" and the "distal end" may include a peripheral portion of the "end" portion instead of only the "end" portion.

The safety needle assembly 100 includes a hub 1, a cannula 2, a collar 3, a protector 4 and a sheath 5. Note an assembly having no protector 4 is also called a "safety needle assembly 100", as described hereinafter.

The cannula 2 is connected with the hub 1 in a general method, for example, using an epoxy resin. The cannula 2 includes a proximal end 21 connected with a distal end of the hub 1 and a distal end 22 having a blade surface 20. Note it is preferable to respectively mold the hub 1, the collar 3, the protector 4 and the sheath 5 as one-piece parts. However, the present embodiment is not limited to the above mentioned method, and a variety of methods can be applied.

The collar 3 is to be fitted with the hub 1 at a predetermined position. Further, the protector 4 is guided by the hub 1 to be fitted with the collar 3 and/or the hub 1, thereby to cover the cannula 2 at the fitting. Moreover, the sheath 5 is to be fitted with the collar 3 so that the sheath 5 can pivot on the collar 3. The detailed explanations will be described hereinafter.

Figure 2:
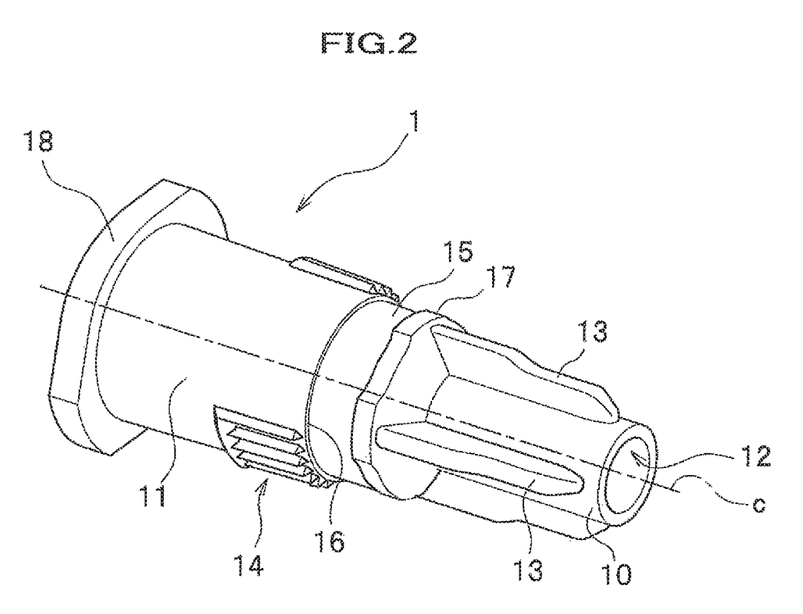
FIG. 2 is a perspective view of a hub which is a component of a safety needle assembly.

As shown in FIG. 2, the hub 1 includes a distal end 10 and a proximal end 11 connected with a syringe (not shown in FIG. 2). Here, a through hole 12 extends along the entire length of the hub 1 in a longitudinal direction (or front-back direction). The through hole 12 has apertures at both distal end 10 and proximal end 11 thereof.

A distal end 21 of the cannula 2 in FIG. 1 is fitted and fixed with the inside of the through hole 12 at the distal end 10 of the hub 1 by using an epoxy resin. Accordingly, a lumen extending along the entire length of the cannula 2 is communicated with the through hole 12 inside the hub 1.

The distal end 10 of the hub 1 comprises a plurality of ribs 13 in a shape resembling a series of steps, with extending in a longitudinal direction. The ribs 13 facilitate the collar 3 to be fitted with the hub 1 in a coaxial manner (or having central axis "c" be coaxial).

A surface of the hub 1 includes a plurality of protrusions 14 projecting from a circumferential outside surface of the hub 1 to an outer side thereof in a radial direction.

Further, a recessed ring region 15 is located at a distal side of the protrusions 14. Accordingly, stage parts 16 and 17 neighboring the recessed ring region 15 have larger external diameters than the recessed ring region 15.

The proximal end 11 of the hub 1 has a flange 18 projecting to an outer side of the hub 1 in a radial direction. The flange 18 is engaged with, for example, a distal end of a syringe body (not shown). The engagement allows the hub 1 to be connected with the syringe body (not shown). This connection step may be performed by a known method, for example, by engaging the flange 18 with a screw (or female screw) located at a distal end of the syringe body (not shown).

Figure 3A:
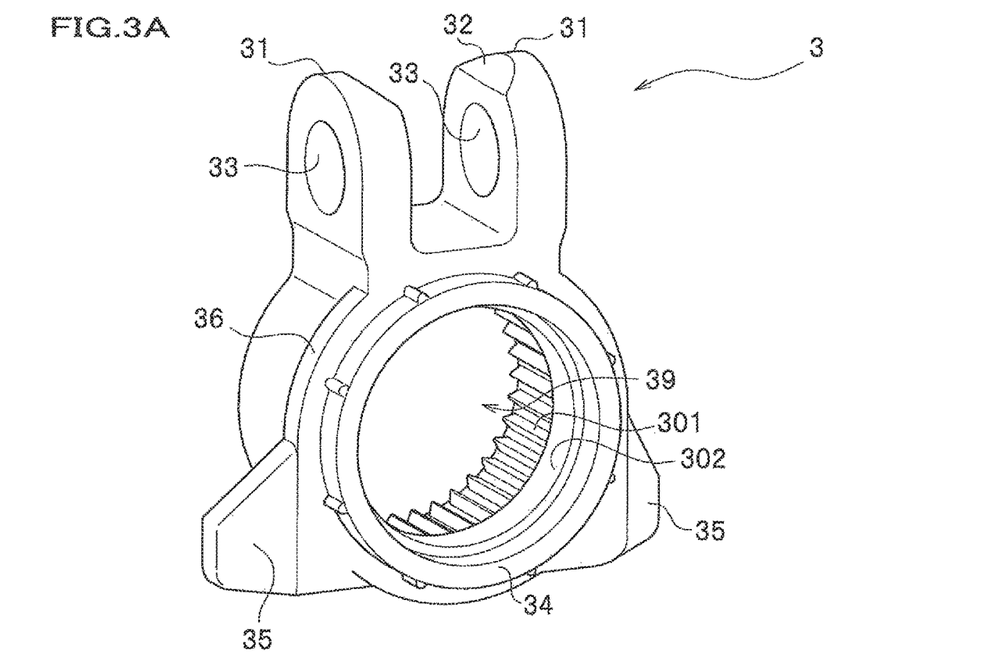
FIG. 3A is a perspective view of a collar which is a component of the safety needle assembly.
Figure 3B:
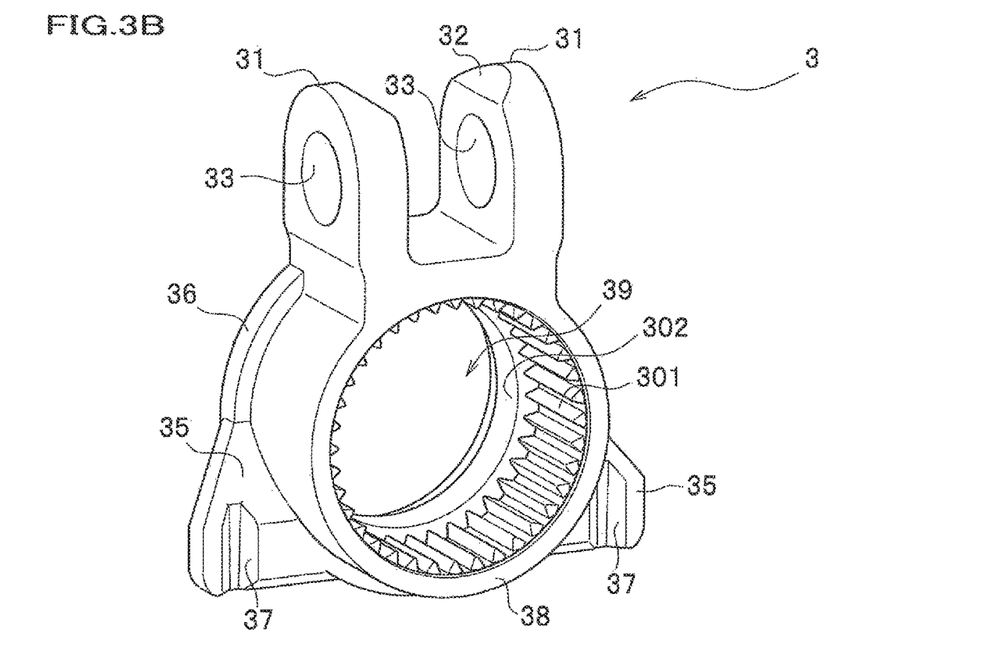
FIG. 3B is a perspective view of the collar, as seen from a back side of the collar in FIG. 3A.

As shown in FIGS. 3A and 3B, the collar 3 has an outline in a circular shape, having a proximal end 38 and a distal end 34. The collar 3 further includes a through hole 39 for the attachment to the hub 1. Here, an inside surface of the collar 3 has a plurality of protrusions 301 projecting to the internal side. Those protrusions 301 projecting to the internal side are engaged with the protrusions 14 of the hub 1. This engagement enables the collar 3 to be unratatably fixed onto the hub 1.

Further, the collar 3 includes a ring-shaped ridge 302 on an inner surface thereof. The ring-shaped ridge 302 is spread over the whole circumference at the inner peripheral side of the through hole 39. Hereby, when the collar 3 is attached to the hub 1, the ring-shaped ridge 302 is seated onto the recessed ring region 15 of the hub 1. Therefore, the ring-shaped ridge 302 has a smaller internal diameter than the external diameters of the two stages 16 and 17 directly neighboring to the recessed ring region 15 of the hub 1. In contrast, the ring-shaped ridge 302 has a substantially equal internal diameter to the external diameter of the recessed ring region 15 of the hub 1. Note the ring-shaped ridge 302 projecting to the internal side in the radial diameter is shown as a consecutive ring-shaped ridge. However, the ring-shaped ridge 302 may be formed, as comprised of a plurality of separated segments, each of which extends along a part of the inner circumference of the collar 3.

The collar 3 has a pair of ears 31 (or sheath attachment part) projecting to the external side in the radial direction. The upper half of the ear 31 has a shape formed by halving a substantially cylindrical shape lying on the side. The ear 31 includes an ear hole 33 with a cylindrical shape to which a pin 540 of the sheath 5 (as described hereinafter) is housed, and a chamfer 32. The chamfer 32 is arranged at an upper portion at the internal side of the ear 31, as shown in FIGS. 3A and 3B. The pin 540 of the sheath 5 passes along the chamfer 32, thereby to be housed in the ear hole 33.

Namely, a pair of ears 31 enables the sheath 5 to be rotatably attached to the collar 3. More specifically, the chamfers 32 facilitate a pair of pins 540 of the sheath 5 to be respectively attached to the pair of ears 31 of the collar 3. Further, when the pair of pins 540 is attached to the pair of ears 31, the pair of ears 31 slightly bends toward the external direction so that the ears 31 are estranged each other. Moreover, a thickness of the ear 31 may be appropriately determined by considering the strength for resistance to damage, and the flexibility for easier attachment of the sheath 5.

The collar 3 includes a ring-shaped ridge 36 projecting to the external side in the radial direction. The ring-shaped ridge 36 is a component for seating the protector 4.

The collar 3 further includes a pair of sheath fixing protrusions 35. The sheath fixing protrusion 35 has a substantially triangle shape, and is arranged at the opposite side of the ear 31. The sheath fixing protrusion 35 further includes a groove 37 which is to be engaged with a wing wall 53 (or cannula fixing part) of the sheath 5.

Figure 4:
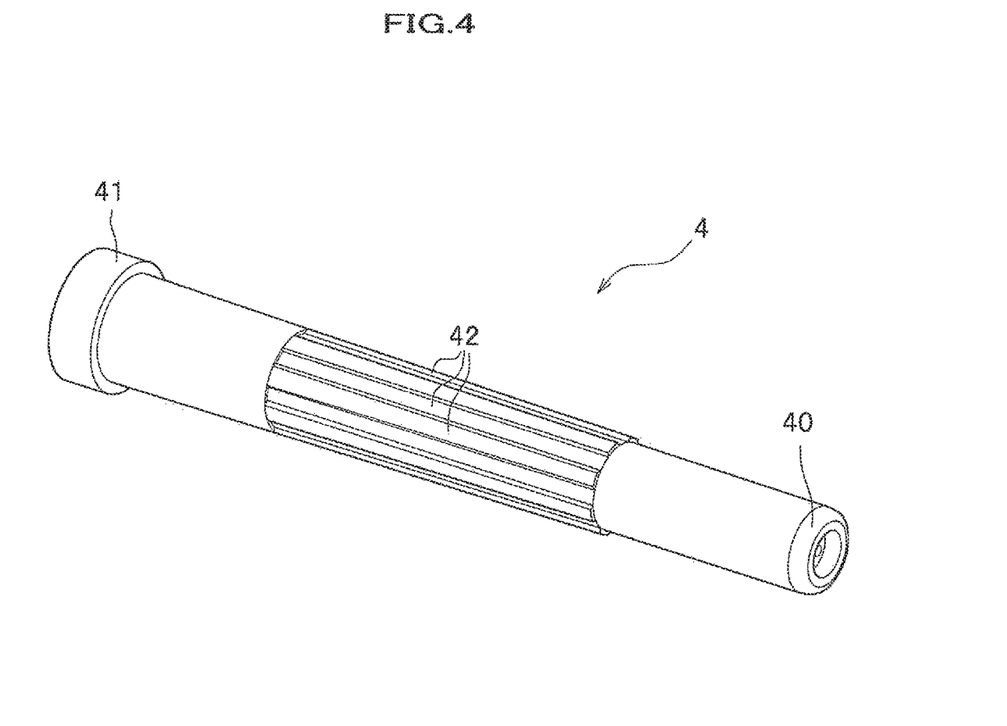
FIG. 4 is a perspective view of a protector which is a component of the safety needle assembly.

As shown in FIG. 4, the protector 4 is formed as a hollow member with an elongated cylindrical shape, including a distal end 40 and a proximal end 41. Preferably, the protector 4 is opened at the proximal end 41 and closed at the distal end 41. A plurality of ribs 42 are arranged in a longitudinal direction at a middle portion of the external surface of the protector 4, so that a user can easily hold the protector 4.

The protector 4 is arranged at the position to cover the cannula 2. This arrangement allows the protector 4 to cover up the distal end of the cannula 2. At that time, the protector 4 is fixed onto the collar 3 and/or the hub 1. Further, the protector 4 can be detachably pivoted so as to expose the distal end 22 of the cannula 2. Note a seating face (not shown) for the collar 3 may be arranged inside the protector 4 at the proximal end 41 thereof.

Figure 5A:
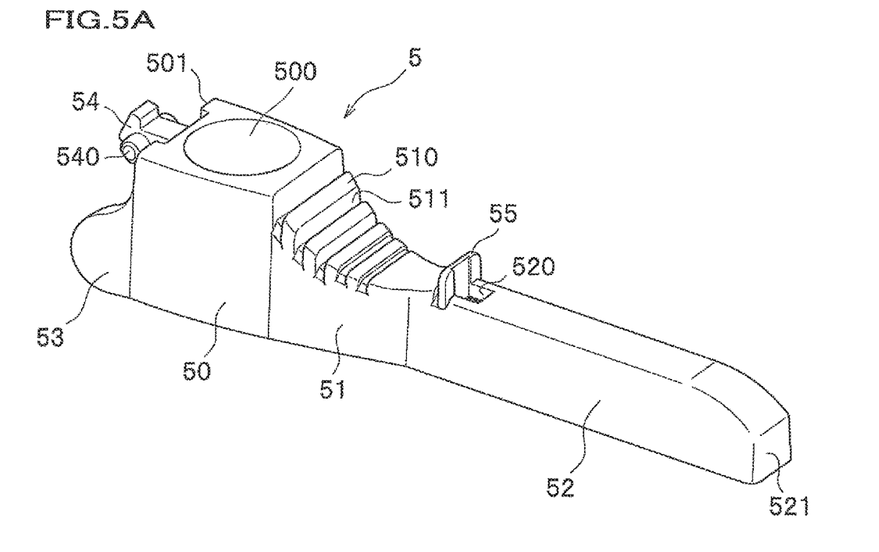
FIG. 5A is a perspective view of a sheath which is a component of the safety needle assembly.
Figure 5B:
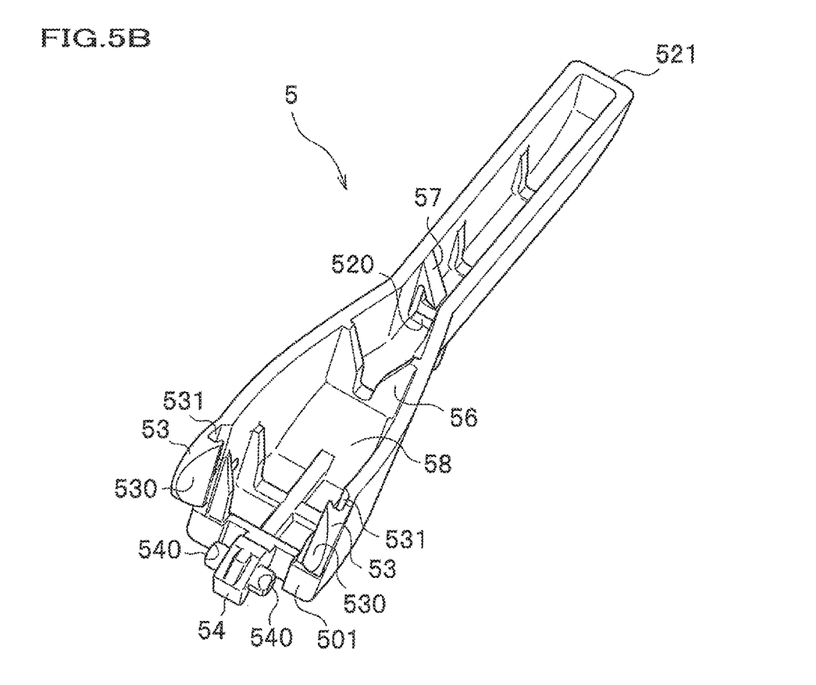
FIG. 5B is a perspective view of the sheath as seen from a bottom side of the sheath in FIG. 5A.

As shown in FIGS. 5A and 5B, the sheath 5 includes a proximal end 501 and a distal end 521, and is formed as an elongated member in the whole body. The sheath 5 includes an opening 58 extending along at least a portion of the longitudinal extent of the sheath 5. The opening 58 is an internal space of the sheath 5. In the present embodiment, the opening 58 of the sheath 5 extends along the entire length in the longitudinal direction. The proximal end 501 is opened in the longitudinal direction of the sheath 5, while the distal end 521 is closed in the longitudinal direction of the sheath 5.

Further, the sheath 5 includes finger guiding parts 50, 51 and a distal part 52, which are composed of a pair of side walls and a back wall. A circular recess 500 is arranged at the back wall of the finger guiding part 50. The circular recess 500 is used as a finger guiding region to which a finger of a user operating the sheath 5 contacts.

The back wall of the finger guiding part 51 is formed as a slope descending to the front portion, in a stepped shape. On the slope, protrusions 510 and recesses 511 are repeatedly arranged so as to increase the friction against a user's finger.

Further, the back wall of the distal part 52 includes a protrusive stopper 55 which prevents the user's finger of pushing the sheath 5 from further moving toward the distal side of the sheath 5. Also, the back wall of the distal part 52 includes a hole 520 which is formed when a locking tab 57 (or cannula fixing part) is molded. Note the stopper 55 is arranged at the vicinity of the center portion in the longitudinal direction, or at the position closer to the distal end side of the sheath 5, so that a larger moment is generated to smoothly pivot the sheath 5, when a user pushes the sheath 5 by a finger.

The sheath 5 includes a collar connection mechanism 54 (or attachment part) having a pair of cylindrical pins 540. The pair of pins 540 is to be attached to the ear holes 33 of the ears 31 at the collar 3, so as to rotatably connect the sheath 5 with the collar 3. Here, each pin 540 is chamfered in order to facilitate the above mentioned connection.

A pair of wing walls 53 is arranged at the proximal end side of the finger guiding part 50. Inside the wing wall 53, a slope 530 is provided in the direction toward the proximal end 501. The slope 530 allows the sheath 5 to be easily attached to the collar 3 (that is, by relatively small force). Further, at the front side of the wing wall 53, is arranged a groove 531 (or cannula fixing part) which fits with the sheath fixing protrusion 35 of the collar 3. Here, it should be noted that when each sheath fixing protrusion 35 of the collar 3 turns to fitting with the corresponding groove 531, the pair of wing walls 53 is to be expanded outside just before the fitting.

An opening 58 of the sheath 5 has a locking tab 57. The locking tab 57 is formed by a punching portion of the back wall of the distal part 52 and protrudes inside from the side wall located inside the opening 58. Here, the locking tab 57 is to be bent when the cannula 2 is introduced into the opening 58. This allows the cannula 2 to move past the side of the locking tab 57. Hereby, the locking tab 57 persistently locks the cannula 2 thus moved past the side of the tab 57 by preventing the cannula 2 from moving back. This locking occurs automatically in the above mentioned movement. In other words, this permanent locking of the cannula 2 fixed inside the sheath 5 can be achieved once the cannula 2 has been introduced into the opening 58 thereby to move past the side of the locking tab 57. Herein, the rib 56 positions the cannula 2 in the left and right direction thereof when the cannula 2 is introduced into the opening 58.

Figure 6:
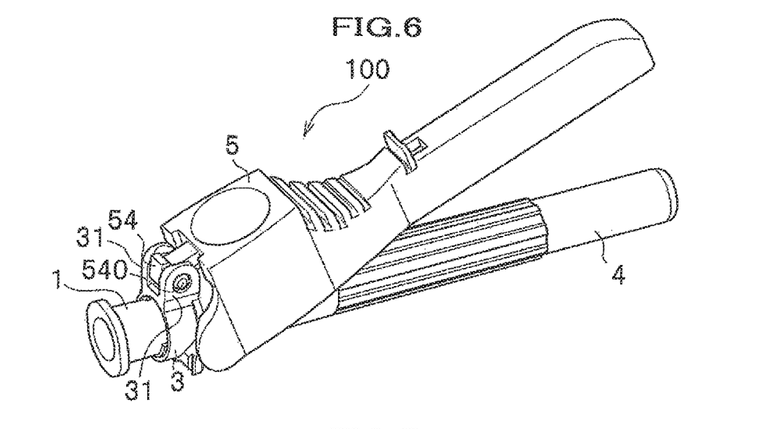
FIG. 6 is a perspective view of the safety needle assembly representing a state that all the components are assembled.

FIG. 6 shows the safety needle assembly 100 thus assembled by the respective components. As described hereinbefore, the safety needle assembly 100 thus assembled may be packaged in a blister packaging or the like in the state of FIG. 6, or may be packaged after the assembly 100 is connected with a syringe (not shown).

Next, referring to FIGS. 6 and 7, a method for using the safety needle assembly 100 will be explained in case a user exposes the cannula 2 from the assembly 100 as shown in FIG. 5.

First, a user pivots the sheath 5 to be apart from the protector 4 so as to remove the protector 4.

Figure 7:
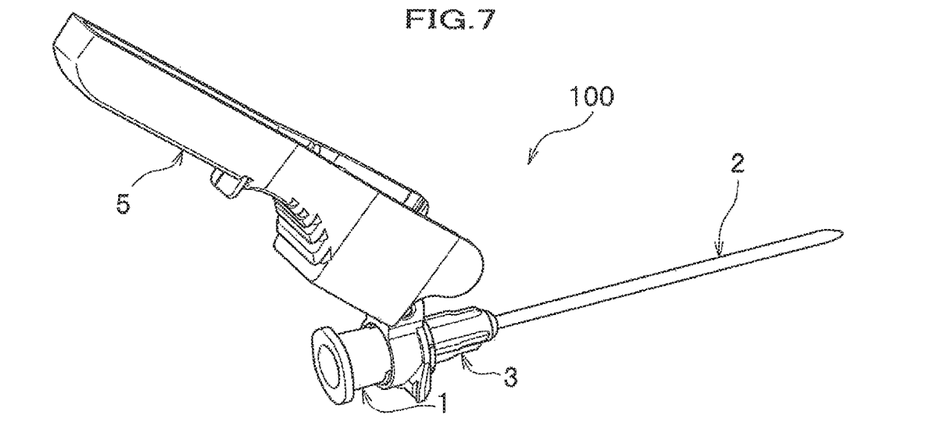
FIG. 7 is a perspective view of the safety needle assembly representing a state ready to be used. This state is prepared by removing a protector from the safety needle assembly in FIG. 6, and exposing a cannula via pivoting the sheath.

After the sheath 5 is pivoted, the user removes the protector 4 and exposes the cannula 2 (see FIG. 7). In this state, the user can use the cannula 2 (for example, to use the cannula 2 for collecting blood from a patient).

Next, referring to FIGS. 7 to 9, a method for using the safety needle assembly 100 will be explained in case a user houses the cannula 2 inside the sheath 5 of the assembly 100 in the state of FIG. 7.

Figure 8:
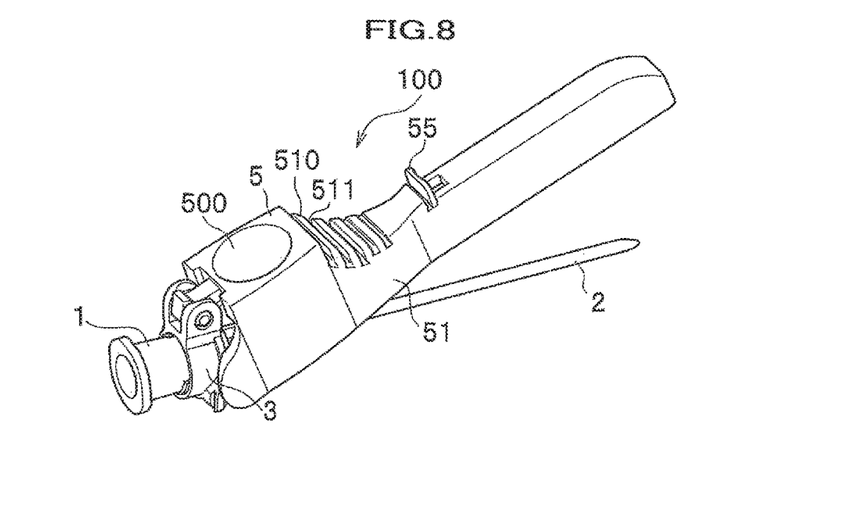
FIG. 8 is a perspective view of the safety needle assembly representing a state just before the cannula is to be housed in the sheath. The state is prepared by pivoting the sheath in the state of the safety needle assembly shown in FIG. 7, after the safety needle assembly has been used.

First, after a user has finished the usage of the cannula 2, the user pivots the sheath 5 toward the cannula 2 thereby to have the safety needle assembly 100 be in the state of FIG. 8.

Figure 9A:
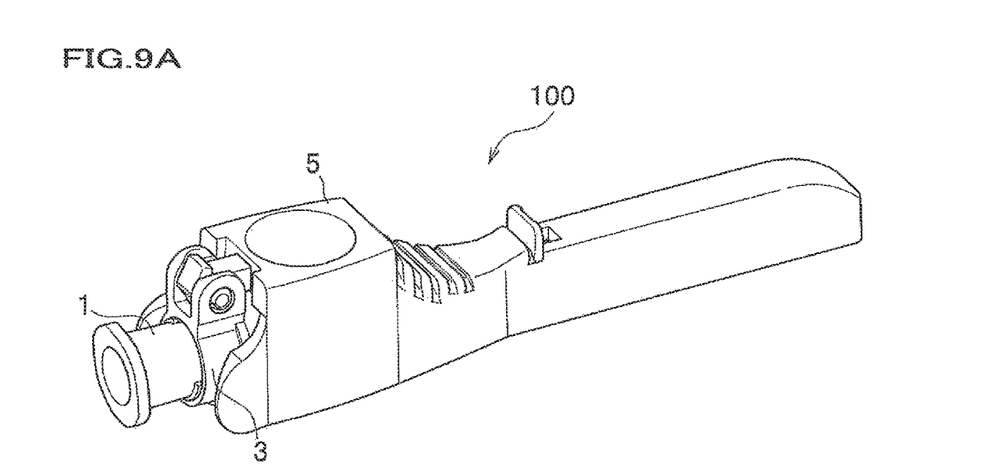
FIG. 9A is a perspective view of the safety needle assembly representing a state that the cannula is housed in the sheath. This state is prepared by a user to push a sheath via a finger, the sheath being in the state of the safety needle assembly shown in FIG. 8.
Figure 9B:
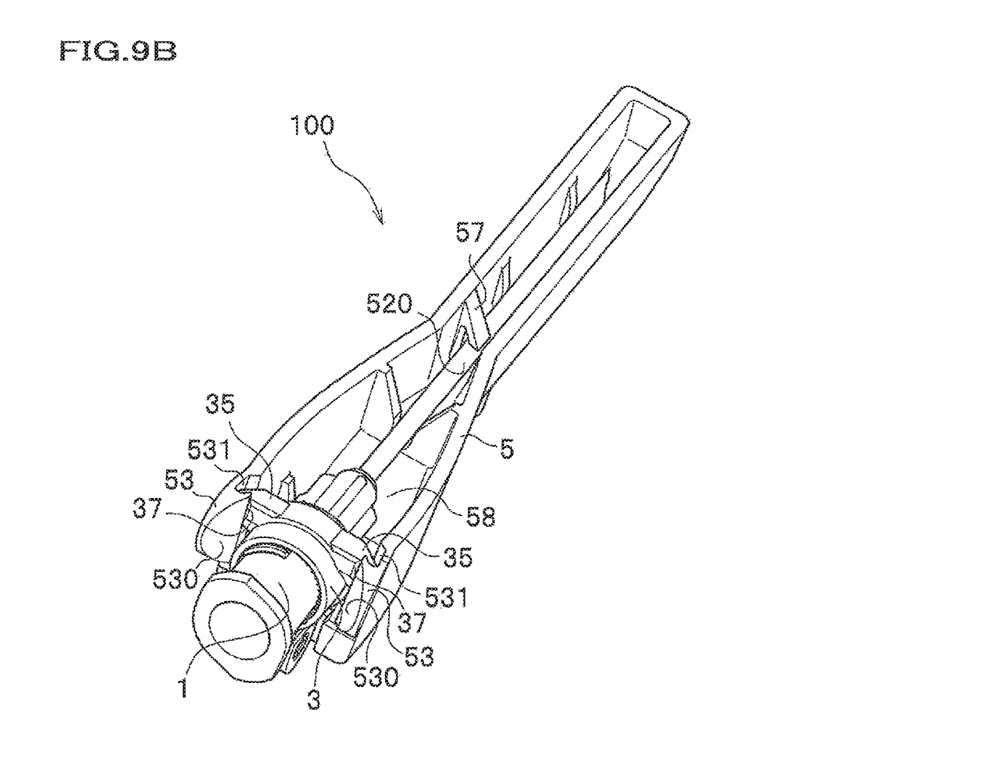
FIG. 9B is a perspective view of the safety needle assembly as seen from a bottom side of the safety needle assembly in FIG. 9A.

Then, the user pushes the back wall of the finger guiding part 51 by a finger against the sheath 5. This allows the sheath 5 to be further pivoted toward the cannula 2 as shown in FIGS. 9A and 9B. The cannula 2 moves past the side of the locking tab 57 to be engaged with the locking tab 57, and the pair of sheath fixing protrusions 35 of the collar 3 is respectively engaged with the corresponding grooves 531 of the sheath 5. Hereby, the cannula 2 is locked inside the sheath 5. That is, at this timing, the cannula 2 is covered by the sheath 5, and further is locked inside the sheath 5.

As described above, the safety needle assembly 100 in the present embodiment enables the high safety due to the mechanism thereof (that is, securing the lower probability that a user erroneously stings the cannula 2 into a body). Further, this also enables the high operability to be realized due to the structure thereof that the sheath 5 has the stopper 55 at the vicinity of the central portion in the longitudinal direction of the sheath 5, or at the position closer to the distal end side than the central portion of the sheath 5. In other words, the above mentioned positioning of the stopper 55 allows a user to push the sheath 5 by a user's finger at a distal side from the fulcrum (or at the position of the pins 540 of the sheath 5), resulting in generation of a larger moment which enables the sheath 5 to be pivoted by relatively smaller force.

Further, the pair of wing walls 52 each having a slope 530 and a groove 531 in the sheath 5 enables the high operability to be realized. That is, the wing walls 53 projecting from the body of the sheath 5 are easy to be bent outward, and the slopes 530 facilitate the sheath fixing protrusions 35 to be introduced of the collar 3 into the grooves 531. Further, the grooves 531 allow the sheath fixing protrusions 35 to be fixed therein. Those mechanisms enable the sheath fixing protrusions 35 of the collar 3 to be fitted and fixed in the grooves 531 of the wing walls 53 of the sheath 5 with relatively small force when a user pushes the sheath 5 by a user's finger.

Moreover, a user can pivot the sheath 5 by pushing not only the slope provided with a plurality of protrusions 510 and recesses 511 having large friction but also the circular recess 500 to which a user's finger easily fits. Accordingly, this allows the high operability to be realized.

Furthermore, the cannula 2 introduced inside the opening 58 of the sheath 5 is locked by the locking tab 57 besides the grooves 531 of the wing walls 53, allowing it less probable that the cannula 2 is exposed after being housed inside the sheath 5. That is, this makes the safety higher. Further, the locking tab 57 is easily molded, allowing the cannula fixing part to be formed at lower cost.

Further, each ear 31 of the collar 3 has a chamfer inside the ear 31, whereby the sheath is attached to the collar 3 through the chamfer, allowing the attachment to need relatively small force.

Further, it is possible to realize that the pair of sheath fixing protrusions 35 of the collar 3 is formed respectively in a substantially triangle having a groove 37, which is made in a simple structure.

Here, the detailed explanations for the embodiments have been completed, while the embodiments of the present invention are not limited to the examples disclosed hereinbefore.

For example, if there are a plurality of cannulas with different lengths, different sheaths 5 corresponding to the respective lengths may be used in the present invention.

Further, a variety of modifications may be appropriately performed with respect to specific structures without departing from the scope of the present invention.

DESCRIPTION OF REFERENCE NUMERALS

1: Hub
2: Cannula
3: Collar
4: Protector
5: Sheath
10: Distal End
11: Proximal End
12: Through Hole
13: Rib
14: Protrusion
15: Recessed Ring Region
16, 17: Stage Part
18: Flange
20: Blade Surface
21: Proximal End
22: Distal End
31: Ear (or Sheath Attachment Part)
32: Chamfer
33: Ear Hole
34: Distal End
35: Sheath Fixing Protrusion
36: Circular Ridge
37: Groove
38: Proximal End
39: Through Hole
40: Distal End
41: Proximal End
42: Rib
50: Finger Guiding Part
51: Finger Guiding Part
52: Distal Part
53: Wing wall (or Cannula Fixing Part)
54: Collar Connection Mechanism (or Attachment Part)
55: Stopper
56: Rib
57: Locking Tab (or Cannula Fixing Part)
58: Opening
100: Safety Needle Assembly
301: Protrusion
302: Ring-shaped Ridge
500: Circular Recess
501: Proximal End
510: Protrusion
511: Recess
520: Hole
521: Distal End
530: Slope
531: Groove (or Cannula Fixing Part)
540: Pin

The invention claimed is:

1. A safety needle assembly with a sheath, comprising:
a hub including a proximal end connecting with a syringe and a distal end;
a cannula including a proximal end connecting with the distal end of the hub, a lumen extending in a longitudinal direction of the cannula, and a distal end;
a collar attached to the hub and having a sheath attachment part; a protector covering the distal end of the cannula by being attached to the hub or the collar, and being detachable to expose the distal end of the cannula; and
an opening partially extending along at least a longitudinal direction of the sheath so as to house the cannula, wherein
the sheath further comprises:
a cannula fixing part housed in the opening and configured to fix the cannula relative to the sheath;
a second attachment part attached to the sheath attachment part of the collar such that, when the protector is detached to expose the distal end of the cannula, the sheath is rotatable relative to the collar to a position in which the sheath houses the cannula;
an outer surface;
a protrusive stopper located on the sheath and projecting away from the outer surface and in a protrusion direction in which, from the position in which the sheath houses the cannula, the sheath is rotatable to reveal the cannula, wherein the protrusive stopper has a plate-like shape, extends in a widthwise direction of the sheath, has a length in the widthwise direction that is substantially the same as a width of a portion of the sheath at which the protrusive stopper is located, and is configured to restrict movement a user's finger pushing the sheath further toward a distal side of the sheath;
a concave recess having a circular perimeter provided on the outer surface of the sheath and used as a finger guiding region configured to be contacted by a finger of a user operating the sheath, the concave recess located proximal to the stopper; and
a curved region located on the outer surface of the sheath between the concave recess and the stopper, the curved region having a plurality of protrusions and recesses formed thereon;
wherein a height of the protrusive stopper, which is a distance that the protrusive stopper projects in the protrusion direction, and the length of the protrusive stopper in the widthwise direction of the sheath, are both greater than a thickness of the protrusive stopper in the longitudinal direction of the sheath.

2. The safety needle assembly as described in claim 1, wherein the sheath cannula fixing part comprises a locking tab which protrudes from a side wall of the opening to an inside of the opening, the locking tab passing the cannula introduced in the opening and then locking the cannula.

3. The safety needle assembly as described in claim 1, wherein the attachment part of the sheath is comprised of cylindrical pins, and a sheath attachment part of the collar is comprised of protruded ears including a pair of through holes each of which houses a respective one of the cylindrical pins, and inside chamfers each of which receives a respective one of the cylindrical pins.

4. The safety needle assembly as described in claim 2, wherein a hole at least partially defined by the protrusive stopper is formed in the outer surface.

\* \* \* \* \*